(12) United States Patent
Heuer et al.

(10) Patent No.: US 7,476,749 B1
(45) Date of Patent: Jan. 13, 2009

(54) CREATINOL-FATTY ACID ESTERS

(75) Inventors: Marvin A. Heuer, Mississauga (CA); Ken Clement, Mississauga (CA); Shan Chaudhuri, Brampton (CA)

(73) Assignee: Multi Formulations Ltd.

( * ) Notice: Subject to any disclaimer, the term of this patent is extended or adjusted under 35 U.S.C. 154(b) by 0 days.

(21) Appl. No.: 11/958,777

(22) Filed: Dec. 18, 2007

(51) Int. Cl.
*C07C 229/00* (2006.01)
(52) U.S. Cl. ....................................... 554/104; 554/107
(58) Field of Classification Search ........................ None
See application file for complete search history.

(56) References Cited

OTHER PUBLICATIONS

Dox Aw, et al. Esterification of creatine. J Biol Chem. 1922;67:671-73.

*Primary Examiner*—Deborah D Carr
(74) *Attorney, Agent, or Firm*—Torys LLP

(57) ABSTRACT

The present invention describes compounds produced from a Creatinol molecule and a fatty acid molecule. The compounds being in the form of Creatinol-fatty compounds bound by an ester linkage, or mixtures thereof produced by reacting Creatinol or derivatives of Creatinol with an appropriate fatty acid in the presence of dichloromethane and an acid catalyst. The administration of such molecules provides supplemental Creatinol with enhanced bioavailability and having additional benefits conferred by the specific fatty acid.

11 Claims, No Drawings

CREATINOL-FATTY ACID ESTERS

FIELD OF THE INVENTION

The present invention relates to structures and methods for the production of Creatinol-fatty acid esters. Another aspect of the present invention relates to a compound comprising a Creatinol molecule bound to a fatty acid, wherein the fatty acid is preferably a saturated fatty acid and is bound to the Creatinol via an ester linkage.

BACKGROUND OF THE INVENTION

Creatinol is closely akin to Creatine, since both molecules contain a guanidino group. It is this guanidine group that binds to the phosphate group in the formation of phosphocreatine. The major difference between Creatinol and Creatine is that the former lacks a carboxylic acid functional group and instead contains a hydroxyl functional group. Where Creatine has a tendency to undergo cyclization to form Creatinine, the Creatinol lacks the carboxylic group that is necessary for the cyclization reaction to take place. Therefore, Creatinol is unable to form the inactive Creatinine, making Creatinol readily available for phosphorylation to form an energetic species like phosphocreatine.

The formation of Creatine esters has been described (Dox A W, Yoder L. Esterification of Creatine. J. Biol. Chem. 1922, 67, 671-673). These are typically formed by reacting Creatine with an alcohol in the presence of an acid catalyst at temperatures from 35° C. to 50° C. as disclosed in U.S. Pat. No. 6,897,334.

Although Creatine esters act to protect Creatine from cyclizing into its inactive form, Creatinine, removal of the ester by esterases, present throughout the body, will again make the Creatine susceptible to inactivation by cyclization. Therefore, a need exists for a Creatine-like molecule that is not as susceptible to conversion into an inactive form and can be easily absorbed by the intestine.

SUMMARY OF THE INVENTION

In the present invention, compounds are disclosed, where the compounds comprise a molecule of Creatinol bound to a fatty acid, via an ester linkage, and having a structure of Formula 1:

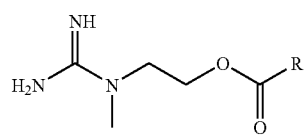

Formula 1 where:

R is an alkyl group, preferably saturated, and containing from about 3 to a maximum of about 21 carbons.

Another aspect of the invention comprises the use of a saturated fatty acid in the production of compounds disclosed herein.

A further aspect of the present invention comprises the use of an unsaturated fatty in the production of compounds disclosed herein.

DETAILED DESCRIPTION OF THE INVENTION

In the following description, for the purposes of explanation, numerous specific details are set forth in order to provide a thorough understanding of the present invention. It will be apparent, however, to one skilled in the art that the present invention may be practiced without these specific details.

The present invention relates to structures and methods for the production of Creatinol-fatty acid compounds bound via an ester linkage. In addition, specific benefits are conferred by the particular fatty acid used to form the compounds in addition to, and separate from, those conferred by the Creatinol substituent.

As used herein, the term "fatty acid" includes both saturated, i.e. an alkane chain as known in the art, having no double bonds between carbons of the chain and having the maximum number of hydrogen atoms, and unsaturated, i.e. an alkene or alkyne chain, having at least one double or alternatively triple bond between carbons of the chain, respectively, and further terminating the chain in a carboxylic acid as is commonly known in the art, wherein the hydrocarbon chain is not less then four carbon atoms. Furthermore, essential fatty acids are herein understood to be included by the term "fatty acid".

The human body can produce all but two of the fatty acids it requires, thus, essential fatty acids are fatty acids that must be obtained from food sources due to an inability of the body to synthesize them, yet are required for normal biological function. The essential fatty acids being linoleic acid and α-linolenic acid.

Examples of saturated fatty acids include, but are not limited to butyric or butanoic acid, caproic or hexanoic acid, caprylic or octanoic acid, capric or decanoic acid, lauric or dodecanoic acid, myristic or tetradecanoic acid, palmitic or hexadecanoic acid, stearic or octadecanoic acid, arachidic or eicosanoic acid, and behenic or docosanoic acid, wherein the aforementioned comprise from at least 4 carbons to 22 carbons in the chain.

Examples of unsaturated fatty acids include, but are not limited to oleic acid, linoleic acid, linolenic acid, arachidonic acid, palmitoleic acid, eicosapentaenoic acid, docosahexaenoic acid and erucic acid, wherein the aforementioned comprise from at least 4 carbons to 22 carbons in the chain.

As used herein, "Creatinol" refers to the chemical 1-(2-hydroxyethyl)-1-methylguanidine.

According to the present invention, the compounds disclosed herein comprise a Creatinol molecule bound to a fatty acid, wherein the fatty acid is preferably a saturated fatty acid. Furthermore, the Creatinol and fatty acid are bound by an ester linkage and having a structure according to Formula 1. The aforementioned compound being prepared according to the reaction as set forth for the purposes of the description in Scheme 1:

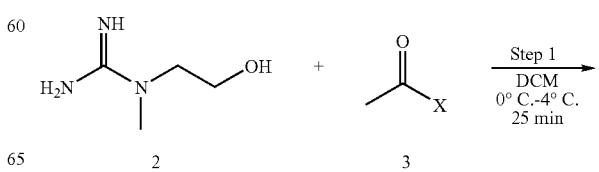

Scheme 1

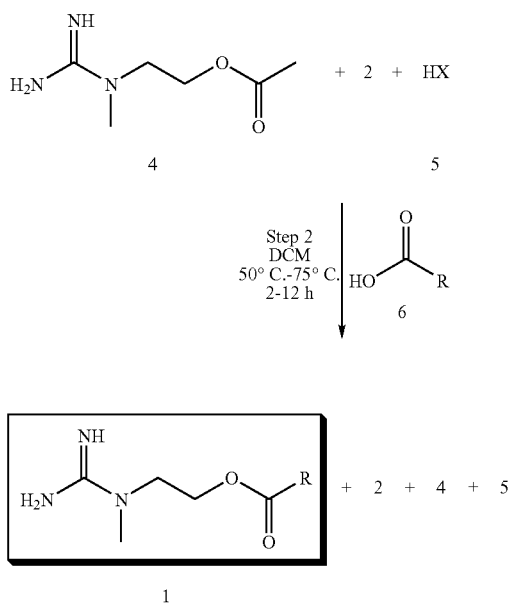

where:
R = alkane or alkene (C = 3 to 21)
X = Cl, Br, F, or I

With reference to Scheme 1, in Step 1 an acidic solution comprising the by product 2-(1-methylguanidino)ethyl acetate (4) an acid (5), corresponding to the halide of the acetyl halide (3), and Creatinol (2) is produced by slowly adding the acetyl halide (3) to Creatinol (2) dissolved in dry Dichloromethane (DCM) at reduced temperatures.

The halide (X) of the acetyl halide (3) is selected from the group consisting of fluorine, chlorine, bromine, and iodine, the preferred method using chlorine or bromine.

The above reaction proceeds under a nitrogen atmosphere at temperatures between about 0° C. to about 4° C. with stirring over a period of about 25 minutes. Preferably, the reactions proceed at about 0° C. for about 25 minutes.

Step 2, all of which takes place under a nitrogen atmosphere, describes the addition of a fatty acid (6) to the resultant acidic solution of Step 1, to form the desired Creatinol-fatty acid ester (1). The addition of the fatty acid (6) takes place at temperatures between about 0° C. to about 4° C. with vigorous stirring. Following complete addition of the fatty acid, the reaction is slowly heated to a temperature between about 50° C. to about 75° C., preferably about 60° C., for between about 2 hours to about 12 hours, before the target ester (1) is isolated and purified, by either fractional distillation of flash chromatography, the preferred purification method being flash chromatography.

The heating of the reaction in Step 2 is maintained, prior to isolation of the target ester, for between about 2 hours to about 6 hours, preferably about 4 hours, if the fatty acid has from about 4 to about 12 carbon atoms, and for between 6 hours and about 12 hours, preferably about 8 hours, if the fatty acid has from about 14 to about 22 carbon atoms.

In various embodiments of the present invention, the fatty acid of (6) is selected from the saturated fatty acid group comprising butyric or butanoic acid, caproic or hexanoic acid, caprylic or octanoic acid, capric or decanoic acid, lauric or dodecanoic acid, myristic or tetradecanoic acid, palmitic or hexadecanoic acid, stearic or octadecanoic acid, arachidic or eicosanoic acid, and behenic or docosanoic acid.

In additional or alternative embodiments of the present invention, the fatty acid of (6) is selected from the unsaturated fatty acid group comprising oleic acid, linoleic acid, linolenic acid, arachidonic acid, palmitoleic acid, eicosapentaenoic acid, docosahexaenoic acid, and erucic acid.

In various embodiments, according to aforementioned, using the saturated fatty acids, the following compounds are produced: 2-(1-methylguanidino)ethyl butyrate, 2-(1-methylguanidino)ethyl hexanoate, 2-(1-methylguanidino)ethyl octanoate, 2-(1-methylguanidino)ethyl decanoate, 2-(1-methylguanidino)ethyl dodecanoate, 2-(1-methylguanidino) ethyl tetradecanoate, 2-(1-methylguanidino)ethyl palmitate, 2-(1-methylguanidino)ethyl stearate, 2-(1-methylguanidino) ethyl icosanoate, and 2-(1-methylguanidino)ethyl docosanoate.

In additional embodiments, according to aforementioned, using the unsaturated fatty acids, the following compounds are produced: 2-(1-methylguanidino) ethyl oleate, (9Z,12Z)-2-(1-methylguanidino)ethyl octadeca-9,12-dienoate, (5Z, 8Z, 11Z,14Z)-2-(1-methylguanidino)ethyl icosa-5,8,11,14-tetraenoate, (Z)-2-(1-methylguanidino)ethyl hexadec-9-enoate, (5Z,8Z,11Z,14Z,17Z)-2-(1-methylguanidino)ethyl icosa-5,8,11,14,17-pentaenoate, (4Z,7Z,10Z,13Z,16Z,19Z)-2-(1-methylguanidino)ethyl docosa-4,7,10,13,16,19-hexaenoate, (Z)-2-(1-methylguanidino)ethyl docos-13-enoate.

The following examples illustrate specific Creatinol-fatty acid esters and routes of synthesis thereof. One of skill in the art may envision various other combinations within the scope of the present invention, considering examples with reference to the specification herein provided.

EXAMPLE 1

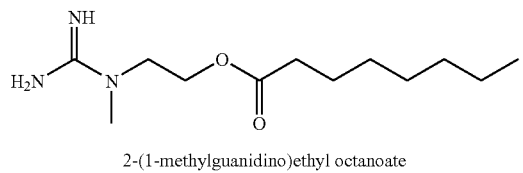

2-(1-methylguanidino)ethyl octanoate

In a dry 3-necked round bottomed flask, containing a magnetic stirrer, equipped with a dropping funnel, a reflux condenser protected from moisture by a calcium chloride filled drying tube and a rubber septum. The dropping funnel is filled with 10.66 mL (150 mmol) of acetyl chloride and 25 mL of dry DCM. The flask is charged with 35.14 g (300 mmol) of Creatinol and 150 mL of dry DCM, and cooled with an ice-water bath to about 0° C., under a nitrogen atmosphere. The acetyl chloride solution is then added slowly with stirring, over a period of 15 minutes, to the Creatinol solution. The solution is stirred for another 10 minutes, after which 13.36 mL (50 mmol) of Octanoic acid is added in one portion and the reaction is slowly heated to about 60° C. for about 4 hours. Then the solution is allowed to cool to room temperature, after which the solvent is removed under reduced pressure to yield the crude ester. The crude ester is then purified by flash chromatography (ethyl acetate/hexanes; 1/3) to yield pure 2-(1-methylguanidino)ethyl octanoate.

EXAMPLE 2

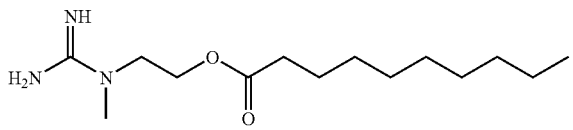

2-(1-methylguanidino)ethyl decanoate

In a dry 3-necked round bottomed flask, containing a magnetic stirrer, equipped with a dropping funnel, a reflux condenser protected from moisture by a calcium chloride filled drying tube and a rubber septum. The dropping funnel is filled with 10.60 mL (125 mmol) of acetyl bromide and 25 mL of dry DCM. The flask is charged with 35.14 g (300 mmol) of Creatinol and 150 mL of dry DCM, and cooled with an ice-water bath to about 0° C., under a nitrogen atmosphere. The acetyl bromide solution is then added slowly with stirring, over a period of 10 minutes, to the Creatinol solution. The solution is stirred for another 15 minutes, after which 9.64 mL (50 mmol) of Decanoic acid is added in one portion and the reaction is slowly heated to about 65° C. for about 6 hours. Then the solution is allowed to cool to room temperature, after which the solvent is removed under reduced pressure to yield the crude ester. The crude ester is then purified by flash chromatography (ethyl acetate/hexanes; 1/5) to yield pure 2-(1-methylguanidino)ethyl decanoate.

EXAMPLE 3

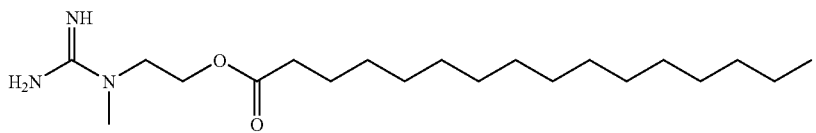

2-(1-methylguanidino)ethyl palmitate

In a dry 3-necked round bottomed flask, containing a magnetic stirrer, equipped with a dropping funnel, a reflux condenser protected from moisture by a calcium chloride filled drying tube and a rubber septum. The dropping funnel is filled with 12.44 mL (175 mmol) of acetyl chloride and 35 mL of dry DCM. The flask is charged with 41.00 g (350 mmol) of Creatinol and 175 mL of dry DCM, and cooled with an ice-water bath to about 0° C., under a nitrogen atmosphere. The acetyl chloride solution is then added slowly with stirring, over a period of 15 minutes, to the Creatinol solution. The solution is stirred for another 10 minutes, after which 15.38 g (60 mmol) of Palmitic acid is added in one portion and the reaction is slowly heated to about 65° C. for about 10 hours. Then the solution is allowed to cool to room temperature, after which the solvent is removed under reduced pressure to yield the crude ester. The crude ester is then purified by flash chromatography (ethyl acetate/hexanes; 2/5) to yield pure 2-(1-methylguanidino)ethyl palmitate.

EXAMPLE 4

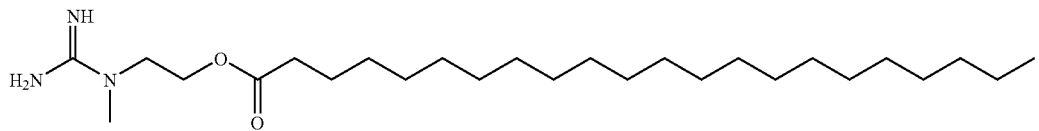

2-(1-methylguanidino)ethyl docosanoate

In a dry 3-necked round bottomed flask, containing a magnetic stirrer, equipped with a dropping funnel, a reflux condenser protected from moisture by a calcium chloride filled drying tube and a rubber septum. The dropping funnel is filled with 12.73 mL (150 mmol) of acetyl bromide and 35 mL of dry DCM. The flask is charged with 35.14 g (300 mmol) of Creatinol and 150 mL of dry DCM, and cooled with an ice-water bath to about 0° C., under a nitrogen atmosphere. The acetyl bromide solution is then added slowly with stirring, over a period of 10 minutes, to the Creatinol solution. The solution is stirred for another 15 minutes, after which 23.84 g (70 mmol) of Docosanoic acid is added in one portion and the reaction is slowly heated to about 65° C. for about 12 hours. Then the solution is allowed to cool to room temperature, after which the solvent is removed under reduced pressure to yield the crude ester. The crude ester is then purified by flash chromatography (ethyl acetate/hexanes; 1/3) to yield pure 2-(1-methylguanidino)ethyl docosanoate.

EXAMPLE 5

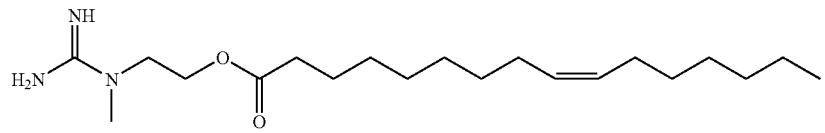

(Z)-2-(1-methylguanidino)ethyl hexadec-9-enoate

In a dry 3-necked round bottomed flask, containing a magnetic stirrer, equipped with a dropping funnel, a reflux condenser protected from moisture by a calcium chloride filled drying tube and a rubber septum. The dropping funnel is filled with 10.66 mL (150 mmol) of acetyl chloride and 25 mL of dry DCM. The flask is charged with 38.07 g (325 mmol) of Creatinol and 150 mL of dry DCM, and cooled with an ice-water bath to about 0° C., under a nitrogen atmosphere. The acetyl chloride solution is then added slowly with stirring, over a period of 15 minutes, to the Creatinol solution. The solution is stirred for another 10 minutes, after which 14.21 mL (50 mmol) of Palmitoleic acid is added in one portion and the reaction is slowly heated to about 55° C. for about 9 hours. Then the solution is allowed to cool to room temperature, after which the solvent is removed under reduced pressure to yield the crude ester. The crude ester is then purified by flash chromatography (ethyl acetate/hexanes; 1/6) to yield pure (Z)-2-(1-methylguanidino)ethyl hexadec-9-enoate.

Thus while not wishing to be bound by theory, it is understood that reacting a Creatinol or derivative of Creatinol with a fatty acid or derivative thereof to form an ester can be used enhance the bioavailability of the Creatinol or derivative Creatinol by improving intestinal absorption, via improved lipophilicity. Furthermore, it is understood that, dependent upon the specific fatty acid, for example, saturated fatty acids form straight chains allowing mammals to store chemical energy densely, or derivative thereof employed in the foregoing synthesis, additional fatty acid-specific benefits, separate from the Creatinol substituent, will be conferred.

EXTENSIONS AND ALTERNATIVES

In the foregoing specification, the invention has been described with a specific embodiment thereof; however, it will be evident that various modifications and changes may be made thereto without departing from the broader spirit and scope of the invention.

The invention claimed is:
1. A compound having the general structure:

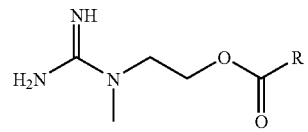

wherein R is selected from the group consisting of alkanes and alkenes;
said alkanes and alkenes having from 3 to 21 carbons.

2. The compound according to claim 1 wherein R is an alkane having 3 to 5 carbons.

3. The compound according to claim 1 wherein R is an alkane having 7 to 9 carbons.

4. The compound according to claim 1 wherein R is an alkane having 11 to 13 carbons.

5. The compound according to claim 1 wherein R is an alkane having 15 to 17 carbons.

6. The compound according to claim 1 wherein R is an alkane having 19 to 21 carbons.

7. The compound according to claim 1 wherein R is an alkene having at least one carbon-carbon double bond, comprising 3 to 5 carbons.

8. The compound according to claim 1 wherein R is an alkene having at least one carbon-carbon double bond, comprising 7 to 9 carbons.

9. The compound according to claim 1 wherein R is an alkene having at least one carbon-carbon double bond, comprising 11 to 13 carbons.

10. The compound according to claim 1 wherein R is an alkene having at least one carbon-carbon double bond, comprising 15 to 17 carbons.

11. The compound according to claim 1 wherein R is an alkene having at least one carbon-carbon double bond, comprising 19 to 21 carbons.

* * * * *